(12) United States Patent
Zhang et al.

(10) Patent No.: US 10,894,771 B2
(45) Date of Patent: Jan. 19, 2021

(54) PREPARATION METHOD OF N-SUBSTITUTED DIBENZO[A,C]CARBAZOLE COMPOUND

(71) Applicant: DALIAN UNIVERSITY OF TECHNOLOGY, Dalian (CN)

(72) Inventors: Sheng Zhang, Dalian (CN); Hengmin Ma, Dalian (CN); Tienan Jin, Dalian (CN); Ming Bao, Dalian (CN)

(73) Assignee: Dalian University of Technology, Dalian (CN)

( * ) Notice: Subject to any disclaimer, the term of this patent is extended or adjusted under 35 U.S.C. 154(b) by 0 days.

(21) Appl. No.: 16/612,025

(22) PCT Filed: Jun. 7, 2018

(86) PCT No.: PCT/CN2018/090256
§ 371 (c)(1),
(2) Date: Nov. 8, 2019

(87) PCT Pub. No.: WO2019/174139
PCT Pub. Date: Sep. 19, 2019

(65) Prior Publication Data
US 2020/0262790 A1    Aug. 20, 2020

(30) Foreign Application Priority Data

Mar. 16, 2018    (CN) .......................... 2018 1 0216474

(51) Int. Cl.
*C07D 209/82*    (2006.01)
(52) U.S. Cl.
CPC .................................. *C07D 209/82* (2013.01)
(58) Field of Classification Search
None
See application file for complete search history.

(56) References Cited

FOREIGN PATENT DOCUMENTS

CN    103772268 A    5/2014

OTHER PUBLICATIONS

Wu, Yongcheng et al., "Palladium catalyzed dual C—H functionalization of indoles with cyclic diaryliodoniums, an approach to ring fused carbazole derivatives"; Organic & Biomolecular Chemistry,vol. 12, Issue No. 48, Oct. 15, 2014, pp. 9777-9780.

Wu, Lijun et al., "Synthesis of dibenzo[a, c]carbazoles from 2-(2-halophenyl)-indoles and iodobenzenes via palladium-catalyzed dual C—H functionalization"; Organic & Biomolecular Chemistry, vol. 15, Issue No. 32, Jul. 27, 2017, pp. 6808-6812.

Cai, Ju et al., "Gold-catalyzed Bicyclization of Diaryl Alkynes: Synthesis of Polycyclic Fused Indole and Spirooxindole Derivatives"; Organic Letters, vol. 20, Issue No. 9, Apr. 13, 2018, pp. 2733-2736.

*Primary Examiner* — Kamal A Saeed
(74) *Attorney, Agent, or Firm* — Muncy, Geissler, Olds & Lowe, P.C.

(57) ABSTRACT

Pharmaceutical and chemical intermediates and relevant chemicals, and relates to a novel preparation method of N-substituted dibenzo[a,c]carbazole compound. O-alkynylaniline and derivatives thereof as raw materials conduct a cascade cyclization reaction in an anhydrous organic solvent in the presence of catalysts, oxidants and additives, and are converted into the N-substituted dibenzo[a,c]carbazole compound. The preparation method of the N-substituted dibenzo[a,c]carbazole compound has fewer reaction steps, low cost of raw material, mild reaction conditions and convenient operation. Moreover, the obtained product has high yield and high purity, fully meets the quality requirements for drug intermediates, and provides favorable conditions for the industrial production.

8 Claims, 14 Drawing Sheets

PREPARATION METHOD OF N-SUBSTITUTED DIBENZO[A,C]CARBAZOLE COMPOUND

TECHNICAL FIELD

The present invention belongs to the technical field of pharmaceutical and chemical intermediates and relevant chemicals, and relates to a simple and novel preparation method of N-substituted dibenzo[a,c]carbazole compound.

BACKGROUND

N-substituted dibenzo[a,c]carbazole compound is an important organic synthesis intermediate for natural products, bioactive molecules and molecules of organic functional material. Efficient and high selective synthesis of the N-substituted dibenzo[a,c]carbazole compound has important practical significance and application value.

The traditional synthesis methods of the carbazole compound mainly include a Graebe-Ullmann reaction, Bucherer carbazole synthesis and Borsche-Drechsel cyclization reaction. Although the methods are well known, the methods are difficult for the application in the synthesis of the N-substituted dibenzo[a,c]carbazole compound. With the development of transition metal-catalyzed reactions, many synthesis methods of the N-substituted dibenzo[a,c]carbazole compound have been reported. The simplest method is the C—N coupling reaction. However, such method requires pre-synthesis of 9-H dibenzo[a,c]carbazole, which limits the application of the method [Duksan Neolux Co. Ltd., Lee B. S., Lee S. H., Moon S. Y., Park J. C., Lee H. Y., 2015, KR101493482(B), 126, 131, 153-155]. Other synthesis methods of the N-substituted dibenzo[a,c]carbazole compound mainly use N-substituted indoles as substrates to construct a target structure through intermolecular or intramolecular reactions.

The intermolecular reactions of the N-substituted indoles involve direct C—H functionalization. Coupling reagents comprise diiodobiaryls [Matsuoka, W., Ito, H., Itami, K., Angew. Chem. Int. Ed., 2017, 56, 12224-12228], diaryliodonium salts [Bhunia S. K., Polley A., Natarajan R., Jana R., Chem. Eur. J., 2015, 21, 16786-16791] and iodobenzenes [Wu L., Deng G., Liang Y., Org. Biomol. Chem, 2014, 12, 9777-9780]. The intramolecular reactions of the N-substituted indoles use biphenyl-substituted N-substituted indoles as substrates to synthesize the N-substituted dibenzo[a,c]carbazole compound through oxidative coupling reactions [Saito K., Chikkade P. K., Kanai M., Kuninobu Y., Chem. Eur. J., 2015, 21, 8365-8368].

Although many synthesis methods of the N-substituted dibenzo[a,c]carbazole compound have been developed, the methods require preformation of an N-containing parent nucleus structure, such as carbazoles or indoles. How to optimize the reaction steps is a difficult problem in the synthesis of such important compound. Cascade cyclization reaction is an effective means to construct a plurality of chemical bonds in one step. However, the synthesis of the N-substituted dibenzo[a,c]carbazole compound by this method has not been reported.

SUMMARY

The present invention provides a novel preparation method of N-substituted dibenzo[a,c]carbazole compound. The method has a short synthesis route, a commercially available substrate, mild conditions, convenient operation and high yield.

The technical solution of the present invention is:

In the preparation method of N-substituted dibenzo[a,c] carbazole compound, o-alkynylaniline derivatives as raw materials are carried out at 80° C.~120° C. for 6-12 hours in an anhydrous organic solvent in the presence of catalysts, oxidants and additives, and are converted, leading to the N-substituted dibenzo[a,c]carbazole compound, with a synthesis route as follows:

$R^1$ = alkyl, Ph   $R^3$ = H, halides, alkyl, $CF_3$
$R^2$ = alkyl, Ph   $R^4$ = H, alkyl, halides, Ph, OMe, $CO_2Me$ wherein $R^1$ is selected from alkyl and Ph;
$R^2$ is selected from alkyl and Ph;
$R^3$ is selected from H, halides, alkyl and $CF_3$;
$R^4$ is selected from H, alkyl, halides, Ph, OMe and $CO_2Me$;
the molar ratio of the o-alkynylaniline derivatives to the catalysts is 1:0.05 to 1:0.2;
the molar ratio of the o-alkynylaniline derivatives to the oxidants is 1:1 to 1:10;
the molar ratio of the o-alkynylaniline derivatives to the additives is 1:0.1 to 1:5;
the molar concentration of the o-alkynylaniline derivatives is 0.01 mmol/mL to 2 mmol/mL.

The organic solvents comprise N,N-dimethylacetamide, toluene, N,N-dimethylformamide, acetonitrile, 1,2-dichloroethane and 1,4-dioxane, and preferably N,N-dimethylacetamide, N,N-dimethylformamide and 1,2-dichloroethane.

The catalysts comprise $Pd(PPh_3)_2Cl_2$, $Pd_2dba_3$, $Pd(OAc)_2$, $PdCl_2$, $Pd(OPiv)_2$ and $Pd(CH_3CN)_4(BF_4)_2$, and preferably $Pd(PPh_3)_2Cl_2$, $PdCl_2$ and $Pd(OPiv)_2$.

The oxidants comprise $Cu(OAc)_2$, $CuCl_2$, $MnO_2$, AgOAc and $O_2$, and preferably $Cu(OAc)_2$, $MnO_2$ and AgOAc.

The additives comprise PivOH, HCOOH, $CH_3COOH$, $NaHCO_3$, $NaHSO_4$, $CH_3COONa$, $K_3PO_4$, $AgSbF_6$ and $AgBF_4$, and preferably PivOH, $CH_3COOH$, $CH_3COONa$ and $AgSbF_6$.

Separation methods comprise recrystallization, column chromatography, etc. The recrystallization method uses solvents such as toluene, alcohol, THF, $CHCl_3$, hexane and acetone; The column chromatography method can use silica gel or alumina as a stationary phase, and use a mixture of polar and nonpolar solvents as an eluent, such as ethyl acetate-petroleum ether, ethyl acetate-hexane, DCM-petroleum ether and methanol-petroleum ether.

The present invention has the beneficial effects that the method has a short synthesis route, mild conditions, simple and convenient operation and possibility of realizing industrialization, and obtains the N-substituted dibenzo[a,c]carbazole product at high yield. The product obtained by the method can have many substituents for further functionalization to obtain functional molecules such as drug intermediates and optical materials.

DETAILED DESCRIPTION

Specific embodiments of the present invention are further described below in combination with accompanying drawings and the technical solution.

The preparation method of the N-substituted dibenzo[a,c]carbazole compound of the present invention has fewer reaction steps, low cost of raw material, mild reaction conditions and convenient operation. Moreover, the obtained product has high yield and high purity, fully meets the quality requirements for drug intermediates, and provides favorable conditions for the industrial production.

The present invention is further described below in combination with the specific embodiments. The embodiments are only used for illustrating the present invention, not used for limiting the scope of the present invention. Simple replacement or improvement made to the present invention by those skilled in the art belongs to the technical solution protected by the present invention.

Embodiment 1

Synthesis of 9-methyl-9H-dibenzo[a,c] carbazole

In a 5 mL reactor, 2-([1,1'-biphenyl]-2-ylethynyl)-N,N-dimethylaniline (0.089 g, 0.3 mmol), PdCl$_2$ (0.005 g, 0.03 mmol), PivOH (0.031 g, 0.3 mmol) and MnO$_2$ (0.078 g, 0.9 mmol) are added; after 1.5 mL of anhydrous N,N-dimethyl acetamide is added and stirred at 80° C. for 12 h, column chromatography (silica gel with 200-300 meshes; eluent, petroleum ether:DCM=1:1) is conducted to provide 0.080 g of 9-methyl-9H-dibenzo[a,c]carbazole with a yield of 95%.

9-methyl-9H-dibenzo[a,c]carbazole

Figure 1:
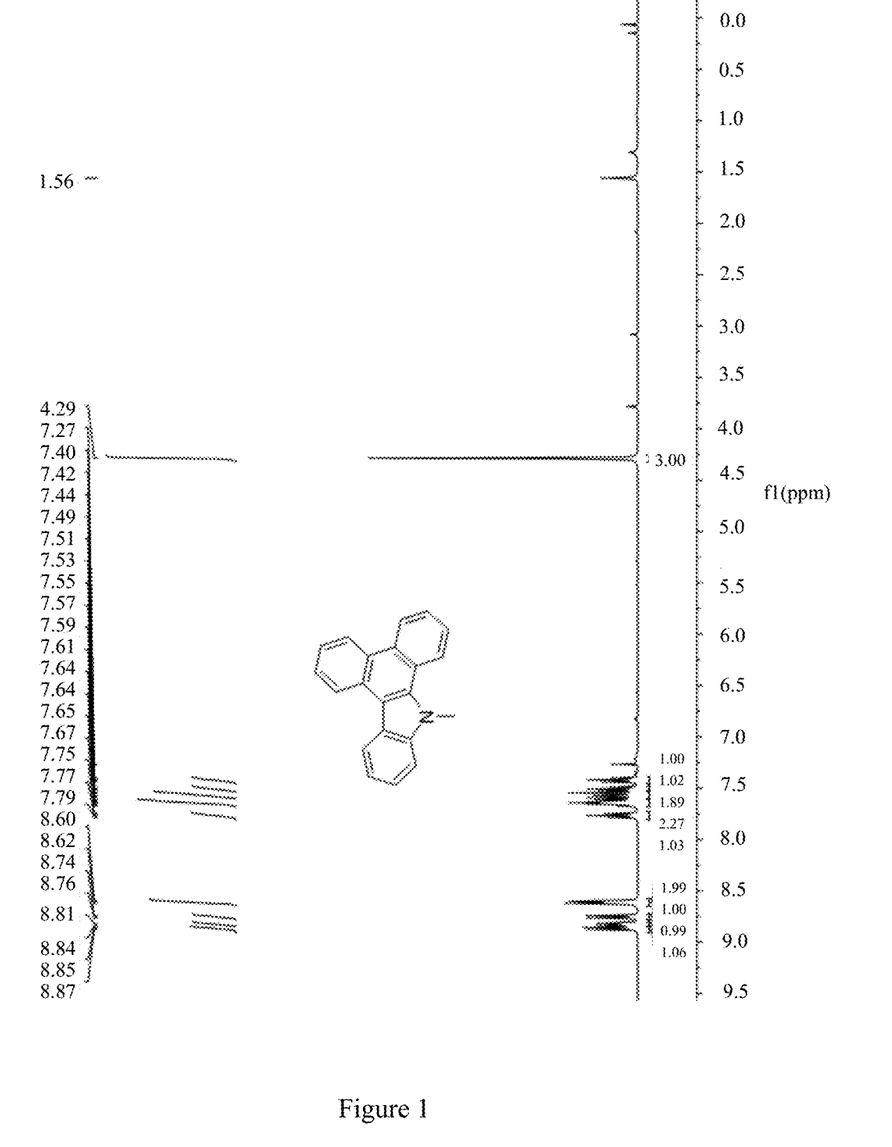
FIG. 1 is a $^1$H NMR of 9-methyl-9H-dibenzo[a,c]carbazole in embodiment 1.
Figure 2:
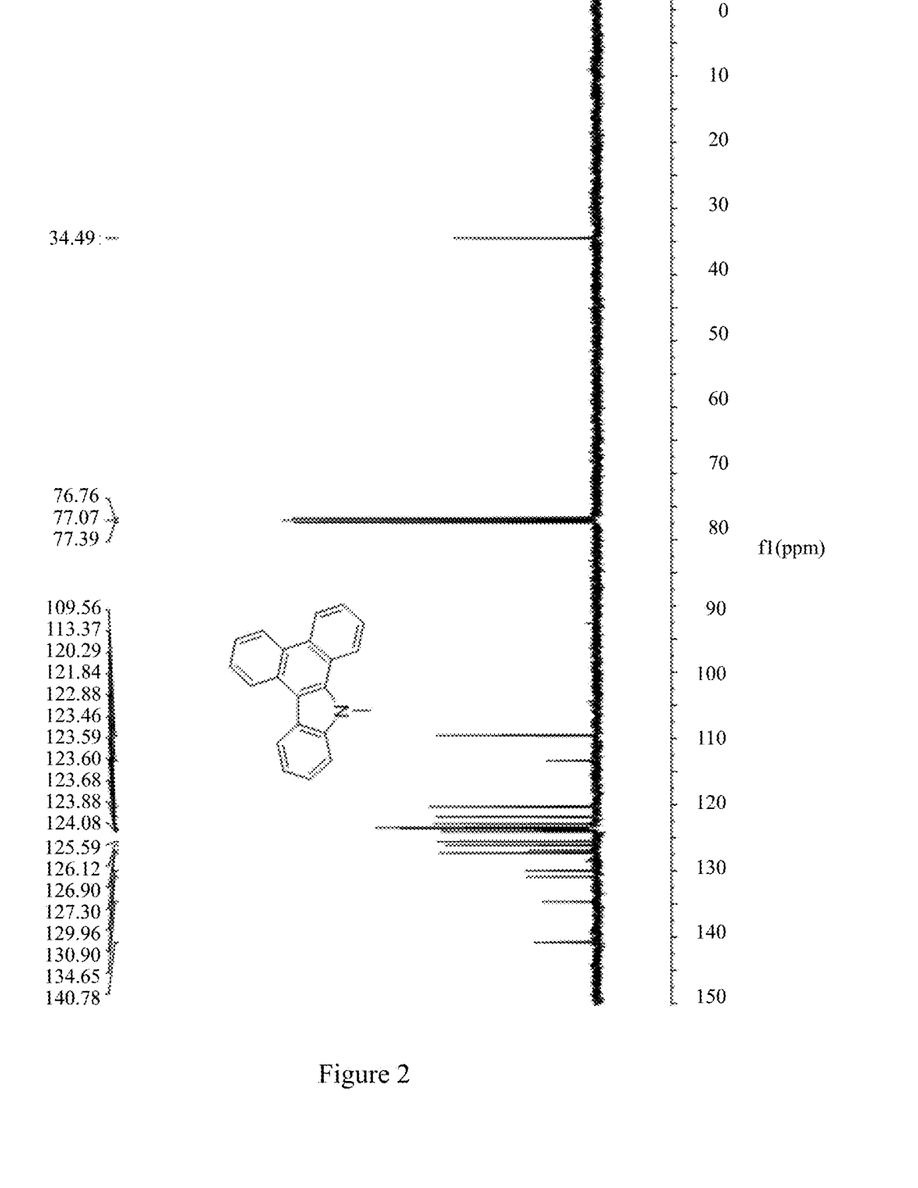
FIG. 2 is a $^{13}$C NMR of 9-methyl-9H-dibenzo[a,c]carbazole in embodiment 1.

Brown solid, $^1$H NMR (400 MHz, CDCl$_3$) δ 4.29 (s, 3H), 7.40 (t, J=8.0 Hz, 1H), 7.51 (t, J=8.0 Hz, 1H), 7.59 (t, J=8.0 Hz, 2H), 7.64-7.67 (m, 2H), 7.77 (t, J=8.0 Hz, 1H), 8.61 (d, J=8.0 Hz, 2H), 8.75 (d, J=8.0 Hz, 1H), 8.83 (d, J=12.0 Hz, 1H), 8.86 (d, J=8.0 Hz, 1H); $^{13}$C NMR (100 MHz, CDCl$_3$) δ 34.5, 109.6, 113.4, 120.3, 121.8, 122.9, 123.5, 123.59, 123.60, 123.7, 123.9, 124.1, 125.6, 126.1, 126.9, 127.3, 130.0, 130.9, 134.7, 140.8; HRMS (EL m/z) calcd for C$_{21}$H$_{15}$N: 281.1192 [M]$^+$; found: 281.1205.

Embodiment 2

Synthesis of 9,12-dimethyl-9H-dibenzo[a,c]carbazole

Operation is the same as that in embodiment 1. 2-([1,1'-biphenyl]-2-ylethynyl)-N,N,4-trimethylaniline reacts to afford 0.067 g of 9,12-dimethyl-9H-dibenzo[a,c]carbazole with a yield of 78%.

9,12-dimethyl-9H-dibenzo[a,c]carbazole

Figure 3:
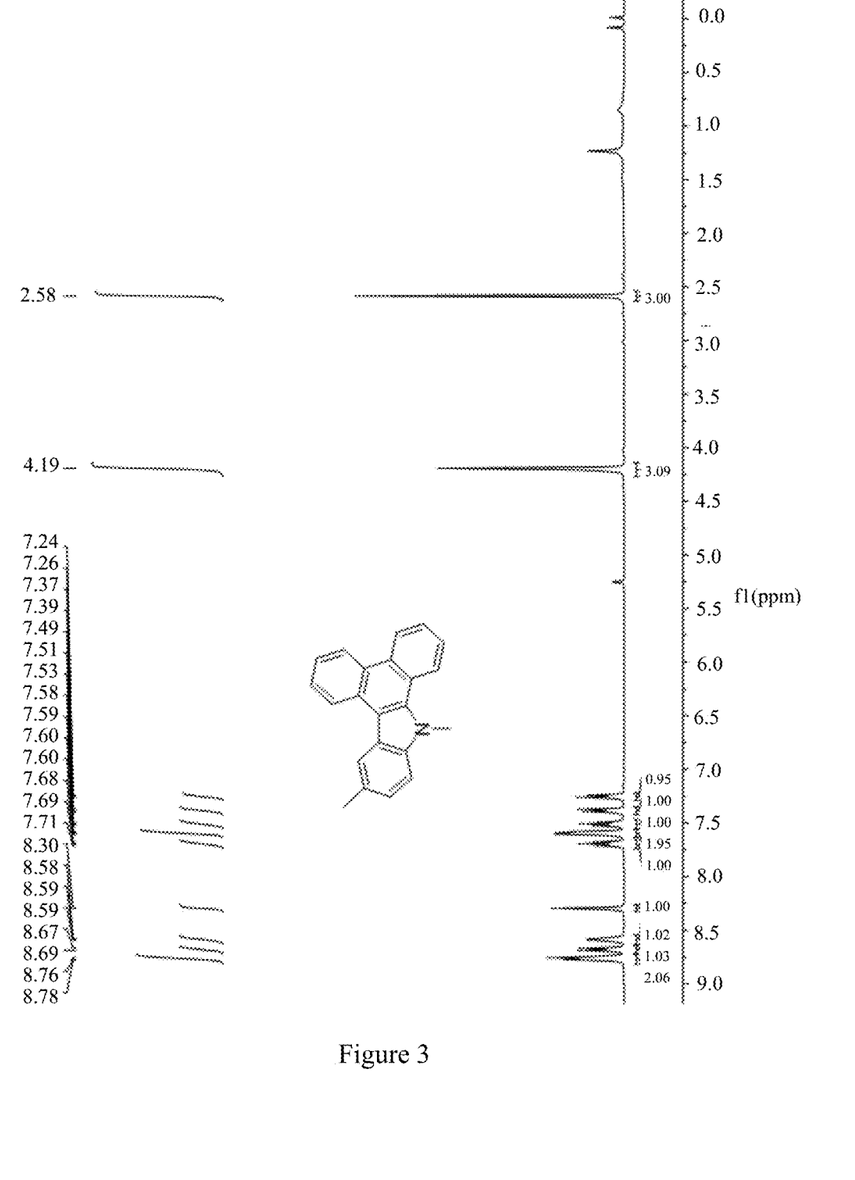
FIG. 3 is a $^1$H NMR of 9,12-dimethyl-9H-dibenzo[a,c]carbazole in embodiment 2.
Figure 4:
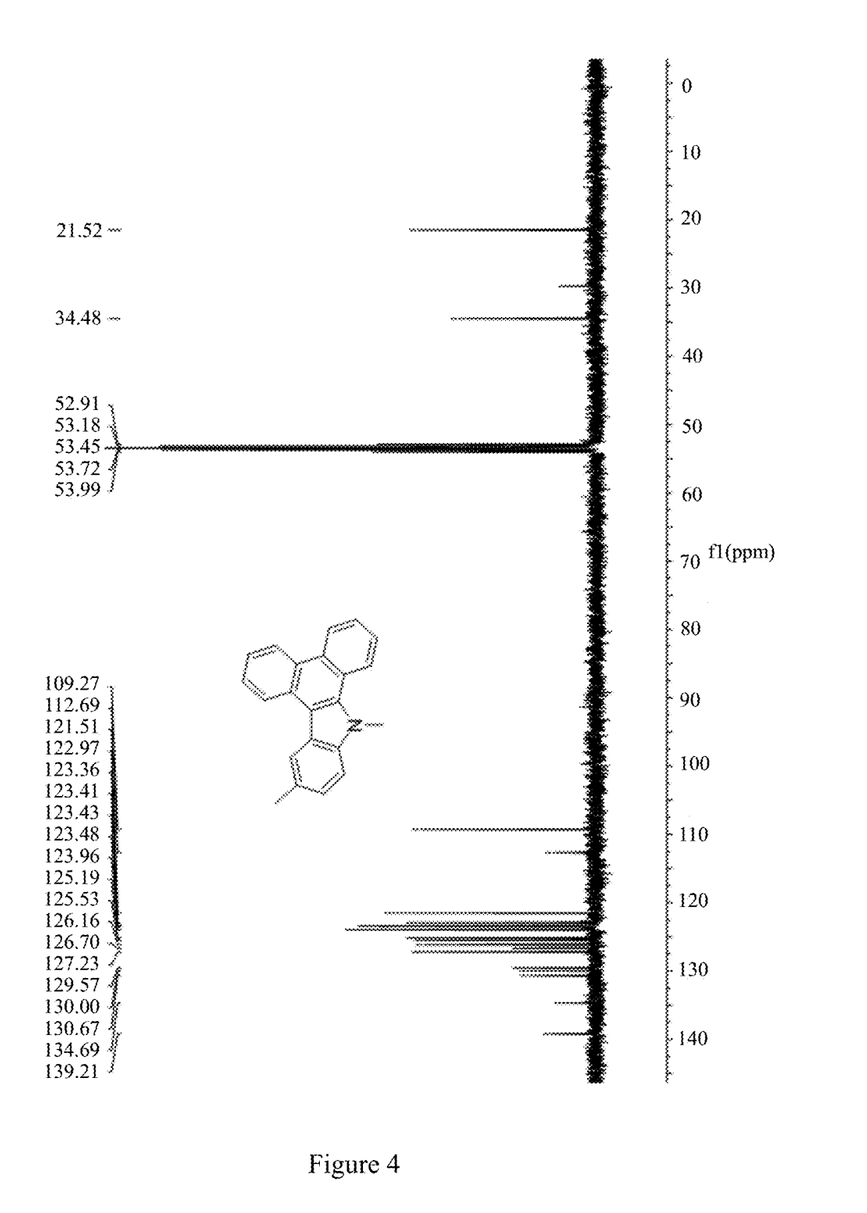
FIG. 4 is a $^{13}$C NMR of 9-methyl-9H-dibenzo[a,c]carbazole in embodiment 2.

Yellowish solid, $^1$H NMR (400 MHz, CD$_2$Cl$_2$) δ 2.58 (s, 3H), 4.14 (s, 3H), 7.25 (d, J=8.0 Hz, 1H), 7.38 (d, J=8.0 Hz, 1H), 7.51 (t, J=8.0 Hz, 1H), 7.58-7.60 (m, 2H), 7.69 (t, J=6.0 Hz, 1H), 8.30 (s, 1H), 8.59 (t, J=4.0 Hz, 1H), 8.68 (d, J=8.0 Hz, 1H) 8.77 (d, J=8.0 Hz, 2H); $^{13}$C NMR (100 MHz, CD$_2$Cl$_2$) δ 21.5, 34.5, 109.3, 112.7, 121.5, 123.0, 123.36, 123.41, 123.43, 123.5, 124.0, 125.2, 125.5, 126.2, 126.7, 127.2, 129.6, 130.0, 130.7, 134.7, 139.2; HRMS (EI, m/z) calcd for C$_{22}$H$_{17}$N: 295.1354 [M]$^+$; found: 295.1369.

Embodiment 3

Synthesis of 11-fluoro-9-methyl-9H-dibenzo[a,c] carbazole

In a 5 mL reactor, 2-([1,1'-biphenyl]-2-ylethynyl)-5-fluoro-N,N-dimethylaniline (0.091 g, 0.3 mmol), PdCl$_2$ (0.005 g, 0.03 mmol), PivOH (0.031 g, 0.3 mmol) and MnO$_2$ (0.078 g, 0.9 mmol) are added; after 1.5 mL of anhydrous N,N-dimethyl acetamide is added and stirred at 80° C. for 6 h, column chromatography (silica gel with 200-300 meshes; eluent, petroleum ether:DCM=5:1) is conducted to afford 0.074 g of 11-fluoro-9-methyl-9H-dibenzo[a,c]carbazole with a yield of 82%.

11-fluoro-9-methyl-9H-dibenzo[a,c]carbazole

Figure 5:
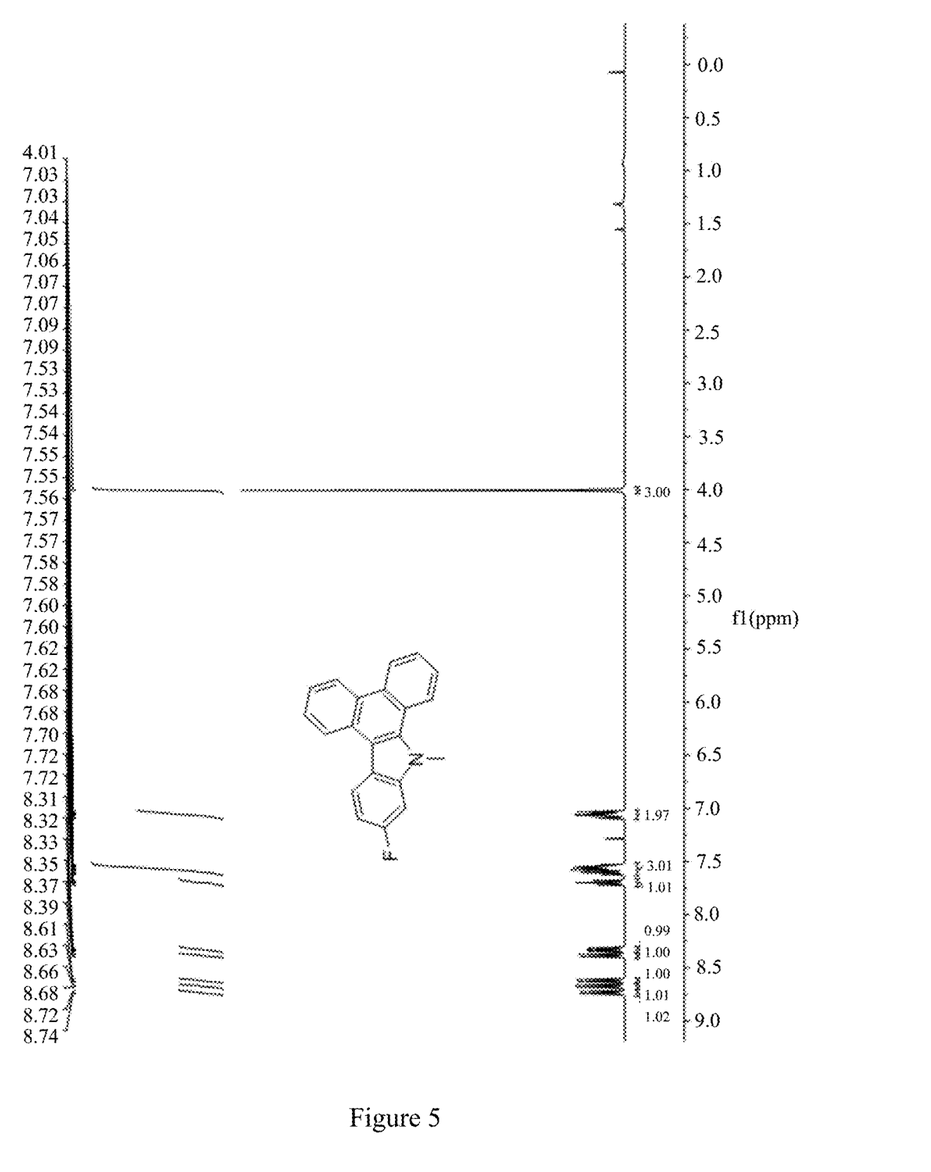
FIG. 5 is a $^1$H NMR of 9-phenyl-9H-dibenzo[a,c]carbazole in embodiment 3.
Figure 6:
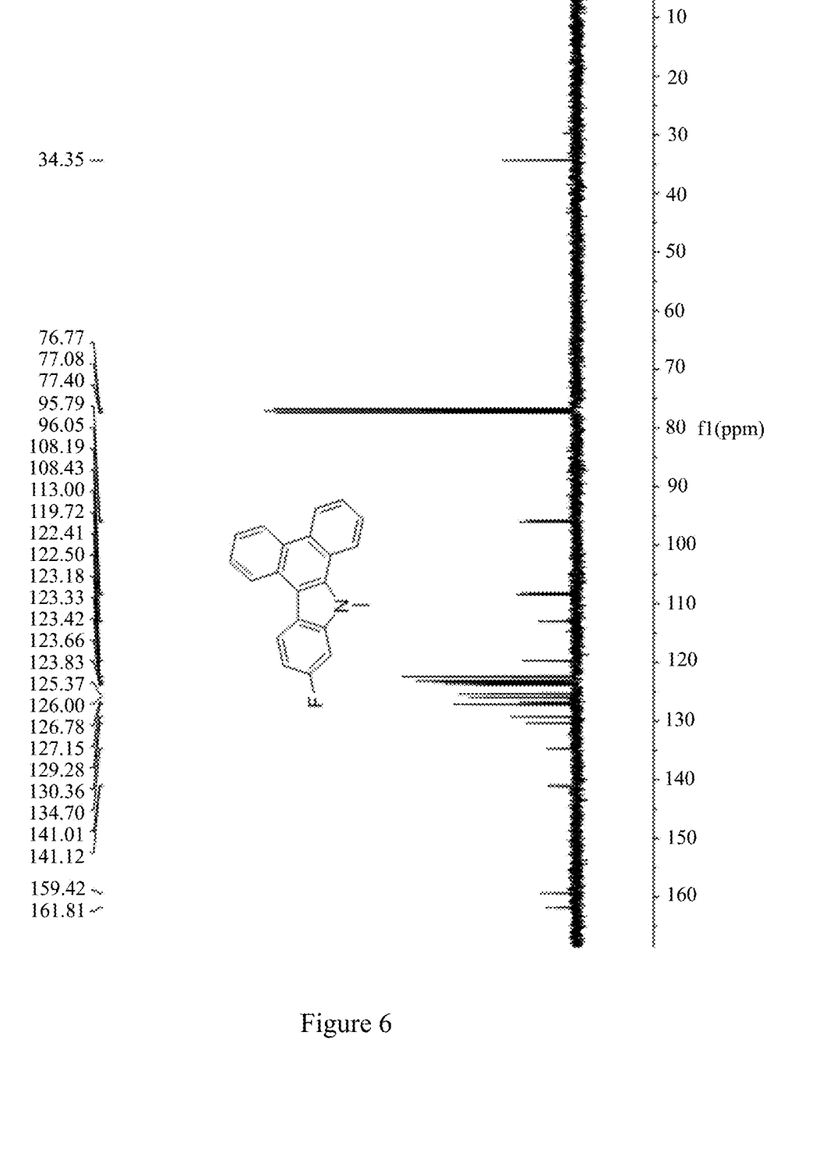
FIG. 6 is a $^{13}$C NMR of 9-phenyl-9H-dibenzo[a,c]carbazole in embodiment 3.

White solid, $^1$H NMR (400 MHz, CDCl$_3$) δ 4.01 (s, 3H), 7.03-7.09 (m, 2H), 7.53-7.62 (m, 3H), 7.70 (t, J=8.0 Hz, 1H), 8.33 (dd, J=8.0, 12 Hz, 1H), 8.38 (d, J=8.0 Hz, 1H), 8.62 (d, J=8.0 Hz, 1H), 8.67 (d, J=8.0 Hz, 1H), 8.73 (d, J=8.0 Hz, 1H); $^{13}$C NMR (100 MHz, CDCl$_3$) δ 34.6, 95.8, 96.1, 108.2, 108.4, 113.0, 119.7, 122.4, 122.5, 123.2, 123.3, 123.4, 123.7, 123.8, 125.4, 126.0, 126.8, 127.2, 129.3, 130.4, 134.7, 141.0, 141.1, 159.4, 161.8; HRMS (EI, m/z) calcd for C$_{21}$H$_{14}$FN: 299.1106 [M]$^+$; found: 299.1105.

Embodiment 4

Synthesis of 9-hexyl-9H-dibenzo[a,c]carbazole

In a 5 mL reactor, 2-([1,1'-biphenyl]-2-ylethynyl)-N,N-dihexylaniline (0.131 g, 0.3 mmol), PdCl$_2$ (0.005 g, 0.03 mmol), PivOH (0.031 g, 0.3 mmol) and MnO$_2$ (0.078 g, 0.9 mmol) are added; after 1.5 mL of anhydrous N,N-dimethyl acetamide is added and stirred at 100° C. for 12 h, column chromatography (silica gel with 200-300 meshes; eluent, petroleum ether:DCM=5:1) is conducted to provide 0.094 g of 9-hexyl-9H-dibenzo[a,c]carbazole with a yield of 89%.

9-hexyl-9H-dibenzo[a,c] carbazole

Figure 7:
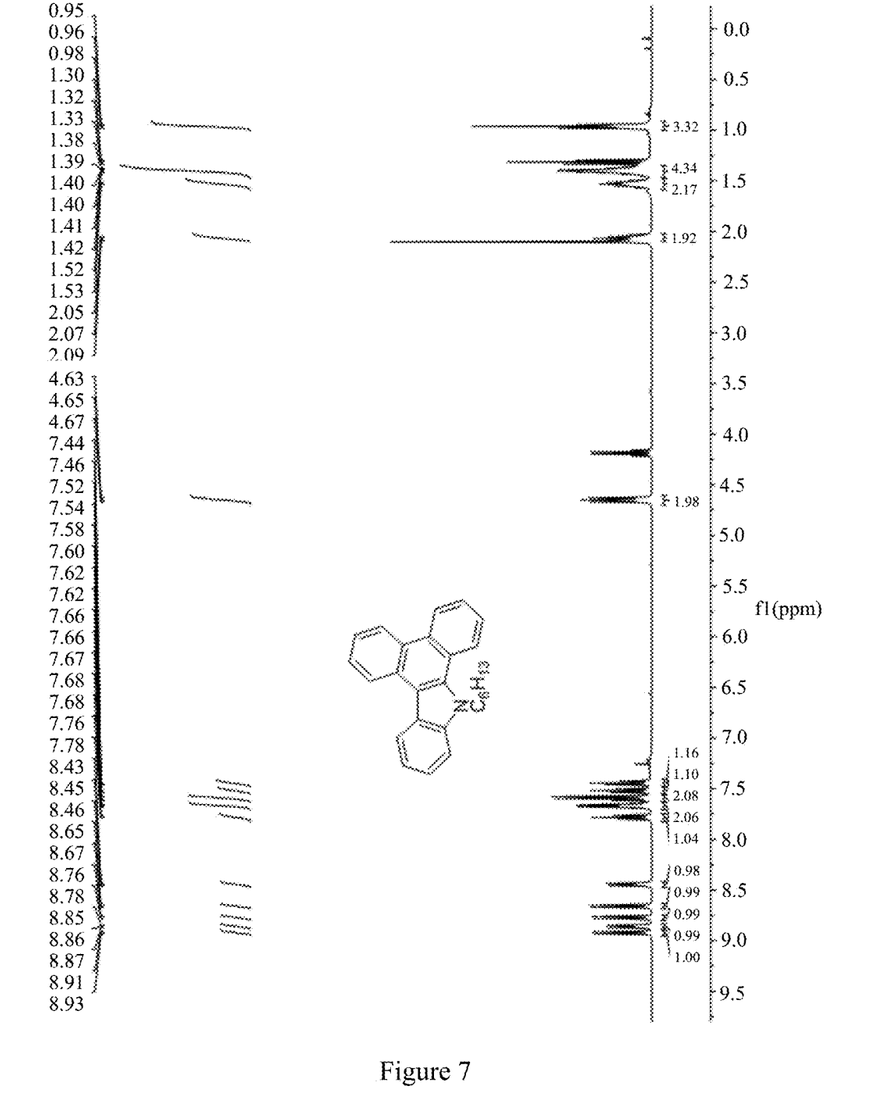
FIG. 7 is a $^1$H NMR of 9-hexyl-9H-dibenzo[a,c]carbazole in embodiment 4.
Figure 8:
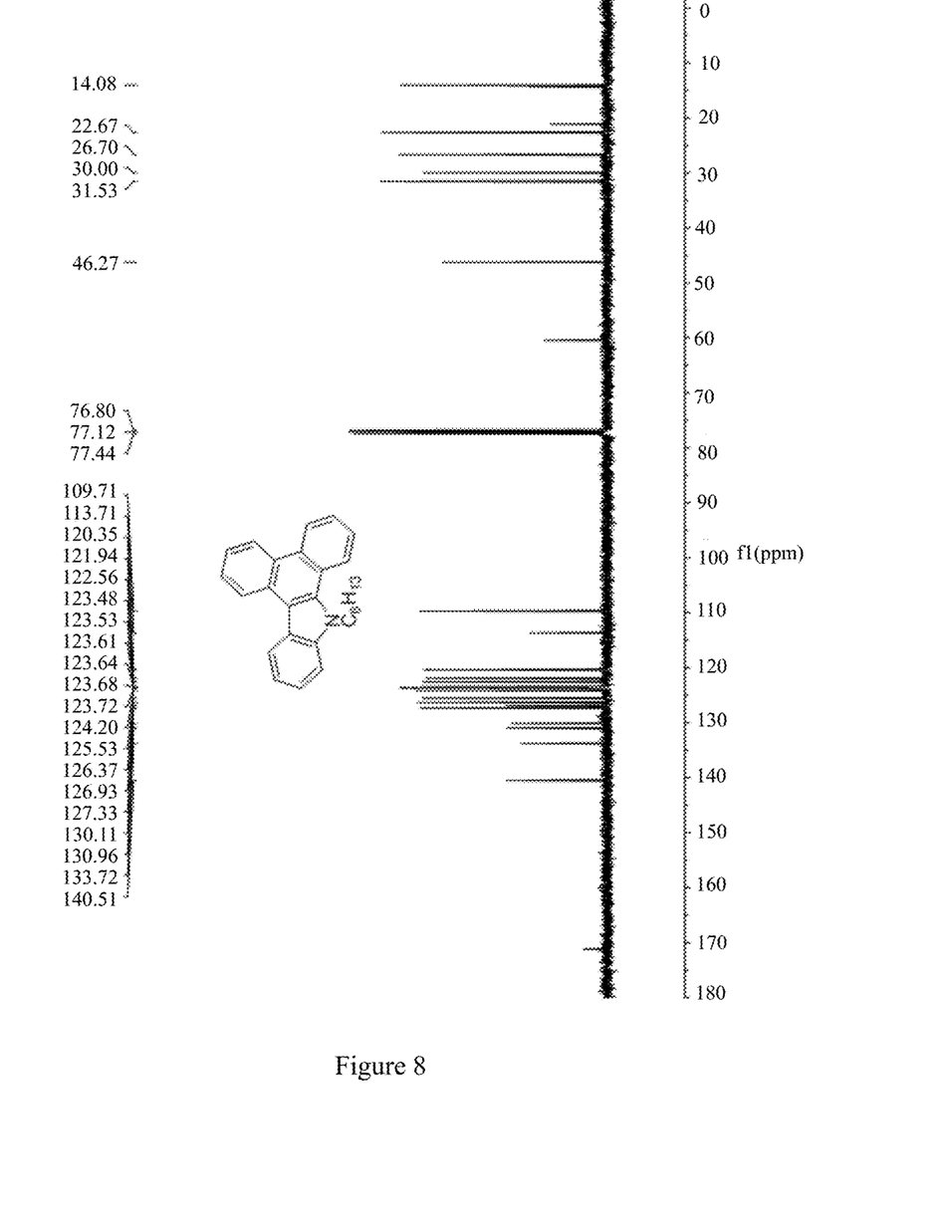
FIG. 8 is a $^{13}$C NMR of 9-hexyl-9H-dibenzo[a,c]carbazole in embodiment 4.

Brown solid, $^1$H NMR (400 MHz, CDCl$_3$) δ 0.96 (t, J=8.0 Hz, 3H), 1.36-1.44 (m, 4H), 1.50-1.57 (m, 2H), 2.03-2.09 (m, 2H), 4.65 (t, J=8.0 Hz, 2H), 7.44 (t, J=8.0 Hz, 1H), 7.52 (t, J=8.0 Hz, 1H), 7.58-7.62 (m, 2H), 7.64-7.69 (m, 2H), 7.78 (t, J=8.0 Hz, 1H), 8.43-8.46 (m, 1H), 8.66 (d, J=8.0 Hz, 1H), 8.77 (d, J=8.0 Hz, 1H), 8.85-8.87 (m, 1H), 8.92 (d, J=8.0 Hz, 1H); $^{13}$C NMR (100 MHz, CDCl$_3$) δ 14.1, 22.7, 26.7, 30.0, 31.5, 46.3, 109.7, 113.7, 120.4, 121.9, 122.6, 123.48, 123.53, 123.61, 123.64, 123.68, 123.72, 124.2, 125.5, 126.4, 126.9, 127.3, 130.1, 131.0, 133.7, 140.5; HRMS (EI, m/z) calcd for C$_{26}$H$_{25}$N: 351.2017 [M]$^+$; found: 351.1984.

Embodiment 5

Synthesis of 9-methyl-12-(trifluoromethyl)-9H-dibenzo[a,c] carbazole

Operation is the same as that in embodiment 3. 2-([1,1'-biphenyl]-2-ylethynyl)-N,N-dimethyl-4-(trifluoromethyl)aniline reacts to give 0.101 g of 9-methyl-12-(trifluoromethyl)-9H-dibenzo[a,c] carbazole with a yield of 97%.

9-methyl-12-(trifluoromethyl)-9H-dibenzo[a,c]carbazole

Figure 9:
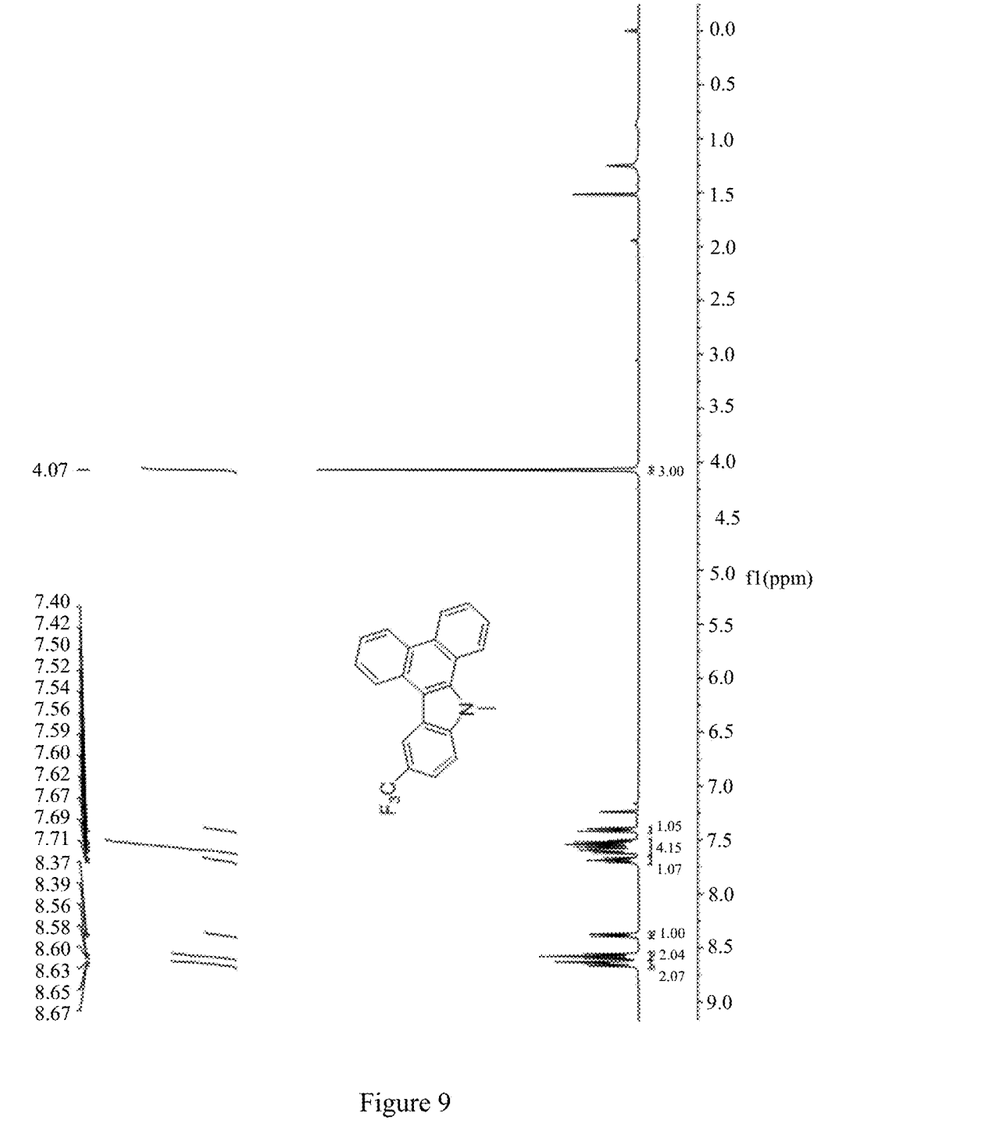
FIG. 9 is a $^1$H NMR of 9-methyl-12-(trifluoromethyl)-9H-dibenzo[a,c]carbazole in embodiment 5.
Figure 10:
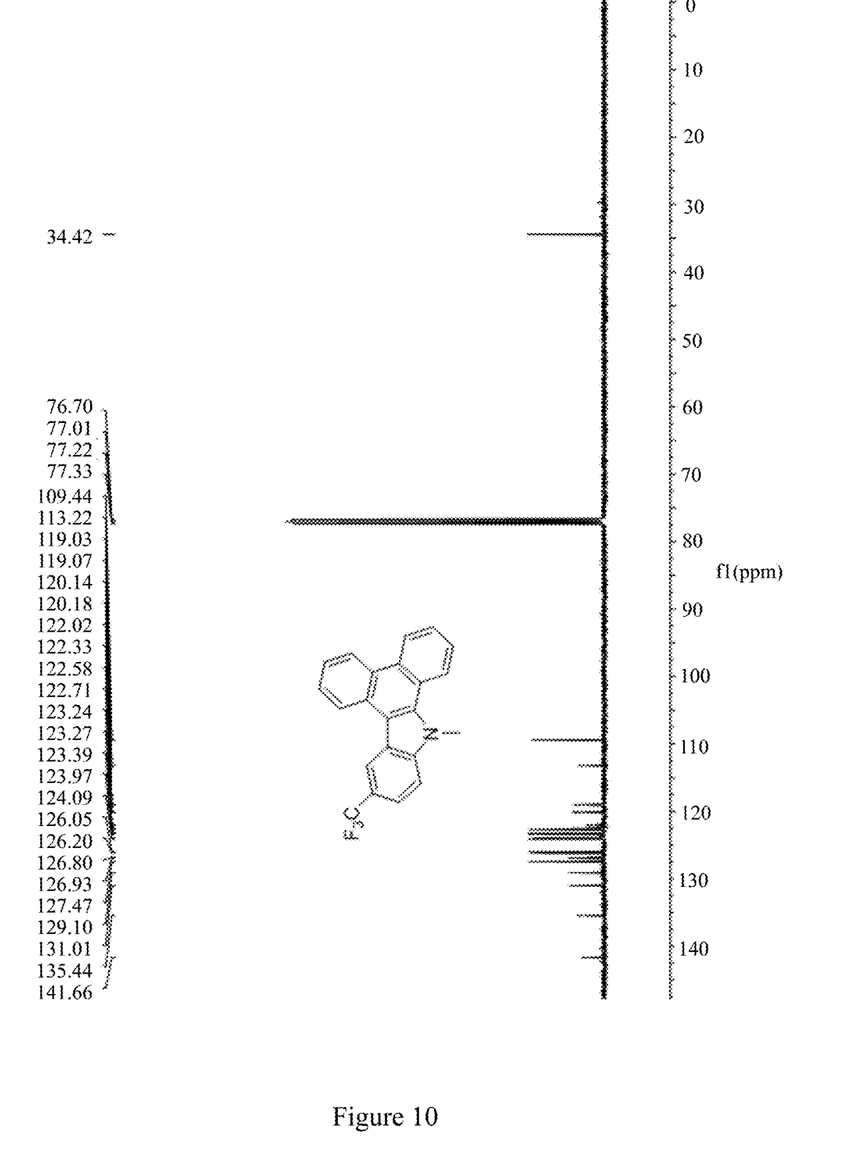
FIG. 10 is a $^{13}$C NMR of 9-methyl-12-(trifluoromethyl)-9H-dibenzo[a,c]carbazole in embodiment 5.

Brown solid, $^1$H NMR (400 MHz, CDCl$_3$) δ 4.07 (s, 3H), 7.41 (d, J=8.0, Hz, 1H), 7.50-7.62 (m, 4H), 7.69 (t, J=8.0 Hz, 1H), 8.38 (d, J=8.0 Hz, 1H), 8.58 (t, J=8.0 Hz, 2H), 8.63-8.67 (m, 2H); $^{13}$C NMR (100 MHz, CDCl$_3$) δ 34.4, 109.4, 113.2, 119.0, 119.1, 120.1, 120.2, 122.0, 122.3, 122.6, 122.7, 123.2, 123.3, 123.4, 124.0, 124.1, 126.1, 126.2, 126.8, 126.9, 127.5, 129.1, 131.0, 135.4, 141.7; HRMS (EL m/z) calcd for C$_{22}$H$_{14}$F$_3$N: 349.1105 [M]$^+$; found: 349.1068.

Embodiment 6

Synthesis of 2-chloro-9-methyl-9H-dibenzo[a,c] carbazole

Operation is the same as that in embodiment 3. N,N-dimethyl-2-((4'-(trifluoromethyl)-[1,1'-biphenyl]-2-yl)ethynyl)aniline reacts to provide 0.082 g of 2-chloro-9-methyl-9H-dibenzo[a,c]carbazole with a yield of 87%.

2-chloro-9-methyl-9H-dibenzo[a,c] carbazole

Figure 11:
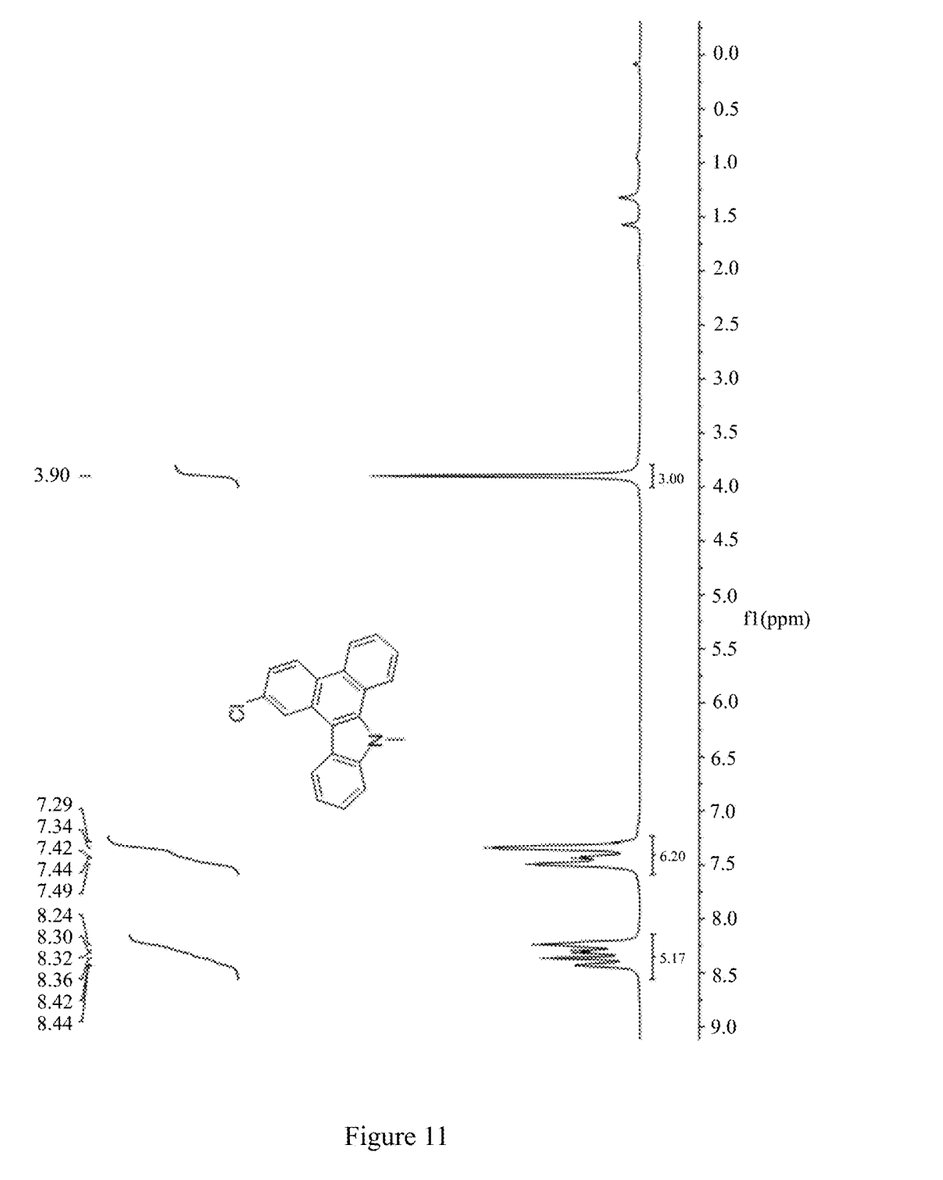
FIG. 11 is a $^1$H NMR of 2-chloro-9-methyl-9H-dibenzo[a,c]carbazole in embodiment 6.
Figure 12:
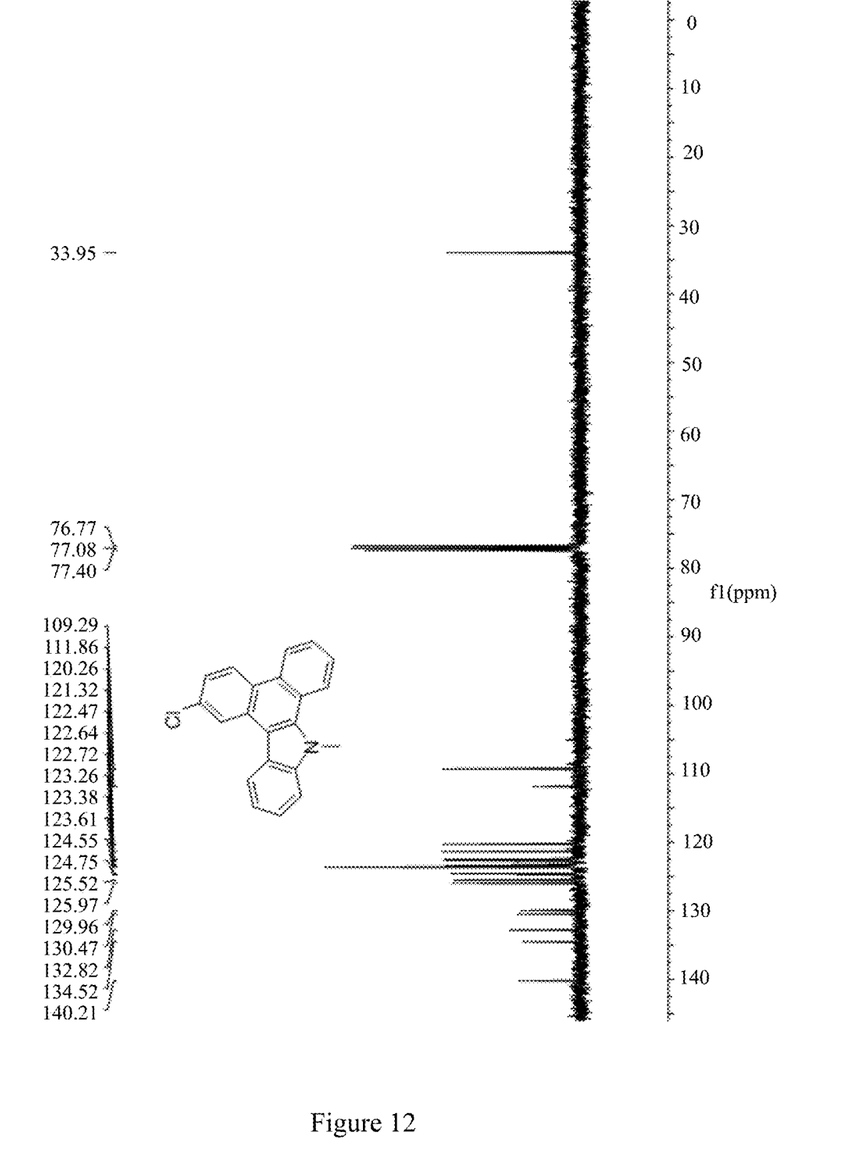
FIG. 12 is a $^{13}$C NMR of 2-chloro-9-methyl-9H-dibenzo[a,c]carbazole in embodiment 6.

Yellowish solid, ¹H NMR (400 MHz, CDCl₃) δ 3.90 (s, 3H), 7.29-7.49 (m, 6H), 8.24-8.44 (m, 5H); ¹³C NMR (100 MHz, CDCl₃) δ 34.0, 109.3, 111.9, 120.3, 121.3, 122.5, 122.6, 122.7, 123.3, 123.4, 123.6, 124.6, 124.8, 125.5, 126.0, 130.0, 130.5, 132.8, 134.5, 140.2; HRMS (EI, m/z) calcd for C₂₁H₁₄ClN: 315.0843 [M]⁺; found: 315.0816.

Embodiment 7

Synthesis of 9-methyl-9H-dibenzo[a,c] carbazole

In a 5 mL reactor, 2-([1,1'-biphenyl]-2-ylethynyl)-N,N-dimethylaniline (0.089 g, 0.3 mmol), PdCl2 (0.005 g, 0.03 mmol), PivOH (0.031 g, 0.3 mmol) and cupric acetate (0.060 g, 0.3 mmol) are added; after 1.5 mL of anhydrous N,N-dimethyl acetamide is added and stirred at 80° C. for 12 h, column chromatography (silica gel with 200-300 meshes; eluent, petroleum ether:DCM=1:1) is conducted to give 0.034 g of 9-methyl-9H-dibenzo[a,c]carbazole with a yield of 40%.

9-methyl-9H-dibenzo[a,c]carbazole

Figure 13:
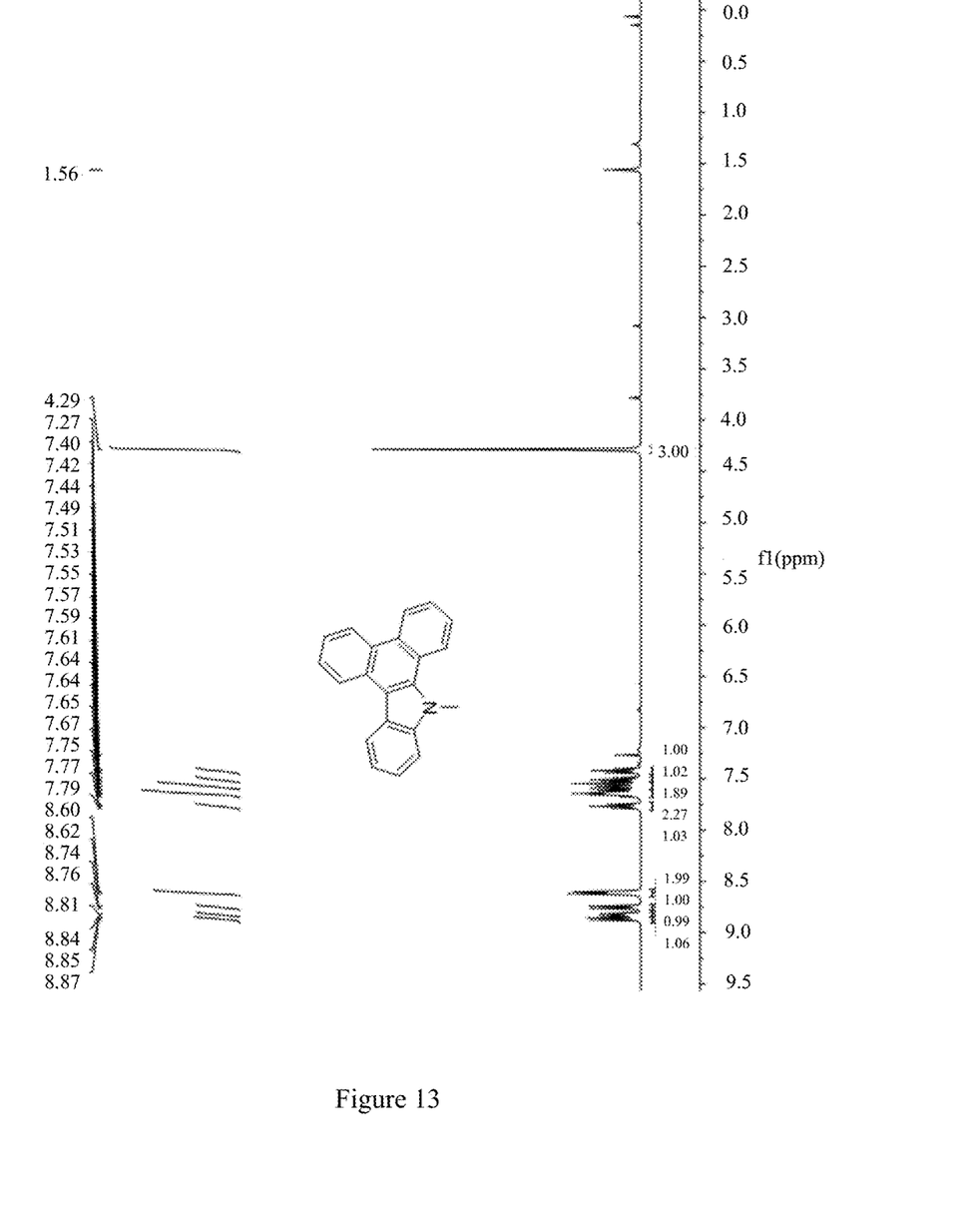
FIG. 13 is a $^1$H NMR of 9-methyl-9H-dibenzo[a,c]carbazole in embodiment 7.
Figure 14:
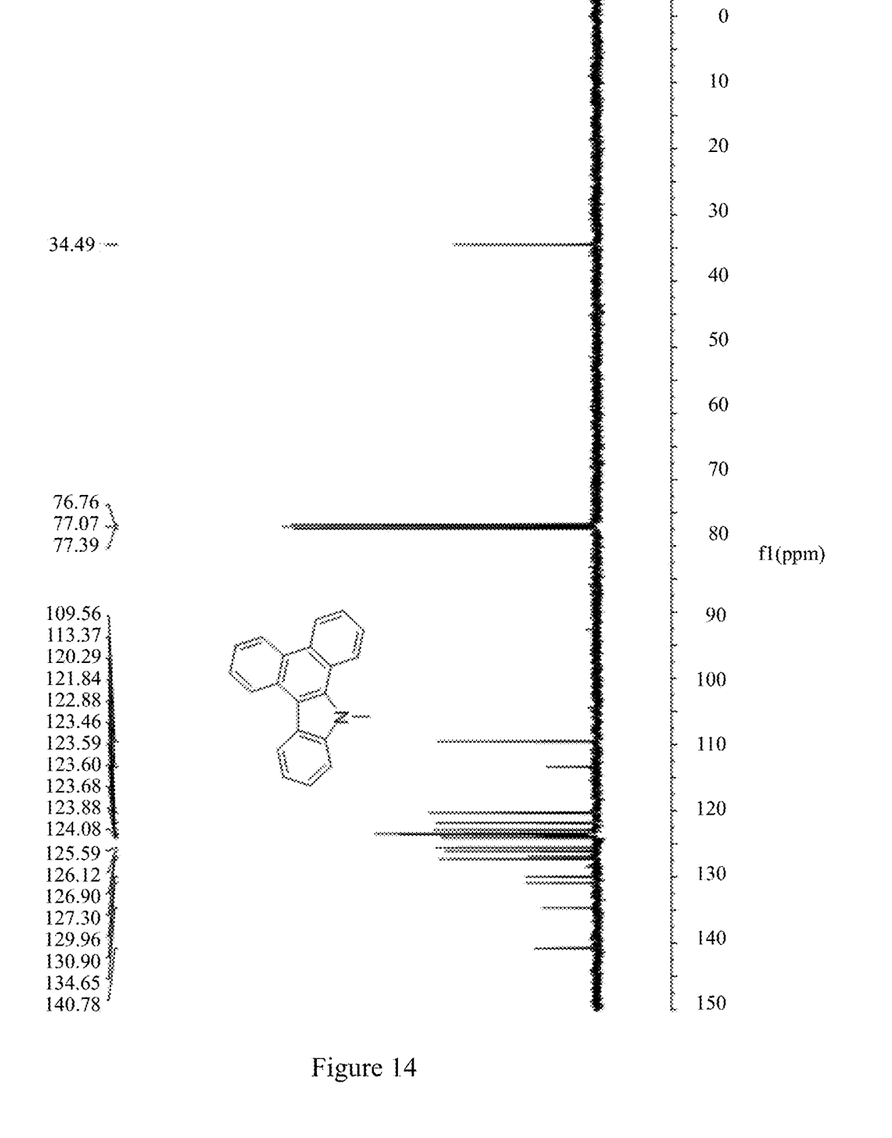
FIG. 14 is a 13C NMR of 9-methyl-9H-dibenzo[a,c]carbazole in embodiment 7.

Brown solid, ¹H NMR (400 MHz, CDCl₃) δ 4.29 (s, 3H), 7.40 (t, J=8.0 Hz, 1H), 7.51 (t, J=8.0 Hz, 1H), 7.59 (t, J=8.0 Hz, 2H), 7.64-7.67 (m, 2H), 7.77 (t, J=8.0 Hz, 1H), 8.61 (d, J=8.0 Hz, 2H), 8.75 (d, J=8.0 Hz, 1H), 8.83 (d, J=12.0 Hz, 1H), 8.86 (d, J=8.0 Hz, 1H); ¹³C NMR (100 MHz, CDCl₃) δ 34.5, 109.6, 113.4, 120.3, 121.8, 122.9, 123.5, 123.59, 123.60, 123.7, 123.9, 124.1, 125.6, 126.1, 126.9, 127.3, 130.0, 130.9, 134.7, 140.8; HRMS (EI, m/z) calcd for C₂₁H₁₅N: 281.1192 [M]⁺; found: 281.1205.

The invention claimed is:

1. A method for preparing N-substituted dibenzo[a,c] carbazole compound, the method comprising using o-alkynylaniline as a raw material, in an anhydrous organic solvent in the presence of catalyst, oxidant and additive, to obtain N-substituted dibenzo[a,c]carbazole compound, with a synthesis route as follows:

$R^1$ = alkyl, Ph  $R^3$ = H, halides, alkyl, CF₃
$R^2$ = alkyl, Ph  $R^4$ = H, alkyl, halides, Ph, OMe, CO₂Me wherein $R^1$ is selected from alkyl and Ph; $R^2$ is selected from alkyl and Ph; $R^3$ is selected from H, halides, alkyl and CF₃; $R^4$ is selected from H, alkyl, halides, Ph, OMe and CO₂Me; a molar ratio of the o-alkynylaniline to the catalyst is 1:0.05 to 1:0.2; a molar ratio of the o-alkynylaniline to the oxidant is 1:1 to 1:10; a molar ratio of the o-alkynylaniline to the additive is 1:0.1 to 1:5; a molar concentration of the o-alkynylaniline is 0.01 mmol/mL to 2 mmol/mL; the additive is one or a mixture of more than one of PivOH, HCOOH, CH₃COOH, NaHCO₃, NaHSO₄, CH₃COONa, K₃PO₄, AgSbF₆ and AgBF₄.

2. The method according to claim 1, wherein the catalyst is one or a mixture of more than one of Pd(PPh₃)₂Cl₂, Pd₂dba₃, Pd(OAc)₂, PdCl₂, Pd(OPiv)₂ and Pd(CH₃CN)₄(BF₄)₂.

3. The method according to claim 1, wherein the oxidant is one or a mixture of more than one of Cu(OAc)₂, CuCl₂, MnO₂, AgOAc and O₂.

4. The method according to claim 1, wherein the organic solvent is one or a mixture of more than one of NN-dimethylacetamide, toluene, N,N-dimethylformamide, acetonitrile, 1,2-dichloroethane and 1,4-dioxane.

5. The method according to claim 3, wherein the organic solvent is one or a mixture of more than two of NN-dimethylacetamide, toluene, N,N-dimethylformamide, acetonitrile, 1,2-dichloroethane and 1,4-dioxane.

6. The method according to claim 2, wherein the additive is one or a mixture of more than one of PivOH, CH₃COOH, CH₃COONa and AgSbF₆; the catalyst is one or a mixture of more than one of Pd(PPh₃)₂Cl₂, PdCl₂ and Pd(OPiv)₂; the oxidant is one or a mixture of more than one of Cu(OAc)₂, MnO₂ and AgOAc; the organic solvent is one or a mixture of more than one of NN-dimethylacetamide, N,N-dimethylformamide, acetonitrile and 1,2-dichloroethane.

7. The method according to claim 3, wherein the additive is one or a mixture of more than one of PivOH, CH₃COOH, CH₃COONa and AgSbF₆; the catalyst is one or a mixture of more than one of Pd(PPh₃)₂C₂, PdCl₂ and Pd(OPiv)₂; the oxidant is one or a mixture of more than one of Cu(OAc)₂, MnO₂ and AgOAc; the organic solvent is one or a mixture of more than one of NN-dimethylacetamide, N,N-dimethylformamide, acetonitrile and 1,2-dichloroethane.

8. The method according to claim 4, wherein the additive is one or a mixture of more than one of PivOH, CH₃COOH, CH₃COONa and AgSbF₆; the catalyst are one or a mixture of more than one of Pd(PPh₃)₂Cl₂, PdCl₂ and Pd(OPiv)₂; the oxidant is one or a mixture of more than one of Cu(OAc)₂, MnO₂ and AgOAc; the organic solvent is one or a mixture of more than one of N,N-dimethylacetamide, N, N-dimethylformamide, acetonitrile and 1,2-dichloroethane.

* * * * *